(12) United States Patent
De Vries et al.

(10) Patent No.: US 7,732,621 B2
(45) Date of Patent: Jun. 8, 2010

(54) PROCESS FOR THE PREPARATION OF ENANTIOMERICALLY ENRICHED INDOLINE-2-CARBOXYLIC ACID

(75) Inventors: Andreas Hendrikus Maria De Vries, Maastricht (NL); Johannes Gerardus De Vries, Maastricht (NL); Friso Bernard Jan Van Assema, Geleen (NL); Ben De Lange, Munstergeleen (NL); Daniel Mink, Eupen (BE); David John Hyett, Sittard (NL); Peter Johannes Dominicus Maas, Puth (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/794,246

(22) PCT Filed: Dec. 22, 2005

(86) PCT No.: PCT/EP2005/014171

§ 371 (c)(1),
(2), (4) Date: Oct. 14, 2008

(87) PCT Pub. No.: WO2006/069799

PCT Pub. Date: Jul. 6, 2006

(65) Prior Publication Data

US 2009/0043112 A1  Feb. 12, 2009

(30) Foreign Application Priority Data

Dec. 28, 2004 (EP) .................................. 04078542

(51) Int. Cl.
*C07D 209/04* (2006.01)
(52) U.S. Cl. ...................................................... 548/492
(58) Field of Classification Search .................. 548/492
See application file for complete search history.

(56) References Cited

FOREIGN PATENT DOCUMENTS

JP       2004-182670       7/2004

OTHER PUBLICATIONS

Wagaw, et al, "Palladium-Catalyzed Coupling of Optically Active Amines with Aryl Bromides," J. Am. Chem. Soc., vol. 119, No. 36, pp. 8451-8458, 1997.
International Search Report dated Apr. 21, 2006.

*Primary Examiner*—Kamal A Saeed
*Assistant Examiner*—Samantha L Shterengarts
(74) *Attorney, Agent, or Firm*—Nixon & Vanderhye P.C.

(57) ABSTRACT

The present invention relates to a process for the preparation of an enantiomerically enriched optionally substituted indoline-2-carboxylic acid or a salt thereof, wherein an enantiomerically enriched chiral ortho-X-substituted phenylalanine compound, wherein X is a leaving group, is subjected to cyclisation, preferably at a temperature of below about 140° C., upon formation of the enantiomerically enriched indoline-2-carboxylic acid compound.

10 Claims, No Drawings

PROCESS FOR THE PREPARATION OF ENANTIOMERICALLY ENRICHED INDOLINE-2-CARBOXYLIC ACID

This application is the US national phase of international application PCT/EP2005/014171 filed 22 Dec. 2005 which designated the U.S. and claims benefit of EP 04078542.0, dated 28 Dec. 2004, the entire content of which is hereby incorporated by reference.

The present invention relates to a process for the preparation of enantiomerically enriched optionally substituted indoline-2-carboxylic acid according to formula (1)

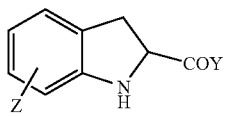

or salts thereof, in which Y is an hydroxyl group, a substituted or non-substituted alkoxy group with 1-10 carbon atoms, a substituted or non-substituted aryloxy group, or an amine residue, and in which Z represents one or more substituents on an aromatic group that are chosen from hydrogen, an hydroxyl group, an optionally substituted cyclic or acyclic aliphatic group with 1-10 carbon atoms, an optionally substituted aliphatic heterocyclic group with 1-10 carbon atoms, an optionally substituted (hetero)aryl group, an optionally substituted alkoxy group with 1-10 carbon atoms, a halogen atom, an amine group, a nitro group, a carboxylic acid, a carboxylic ester, a carboxylic amide, nitril or trifluoromethyl group.

Enantiomerically enriched indoline-2-carboxylic acids according to formula (1) are important intermediates for pharmaceutical products, in particular in the preparation of angiotensin I converting enzyme inhibitors (ACE), which are used for the treatment of high blood pressure (hypertension). Optically active (S)-indoline-2-carboxylic acid, for instance, can be used in the preparation of [2S-[1[R*(R*),2α,3aβ,7aβ]]-1-[2-[[1-(ethoxycarbonyl)butyl]amino]-1-oxopropyl]octahydro-1H-indole-2-carboxylic acid, also known under the tradename Perindopril, that is useful as an antihypertensive (ACE inhibitor) or cardiotonic active ingredient. Other useful applications are, for example, Pentopril and Indolapril.

EP 0 937 714 A1 discloses a process for the preparation of optically active indoline-2-carboxylic acid by contacting a mixture of the enantiomers of N-acyl-indoline-2-carboxylic acid with an optically active resolving agent, by liberating the optically active N-acyl-indoline-2-carboxylic acid from the resulting diastereomeric salt and, thereafter, de-acylating the optically active N-acyl-indoline-2-carboxylic acid upon formation of optically active indoline-2-carboxylic acid.

A disadvantage of the known process is that said process is rather elaborate and that an additional step is needed to separate the two enantiomers in the racemic mixture of N-acyl-indoline-2-carboxylic acid. Ultimately, the desired optically active indoline-2-carboxylic acid can be obtained in a yield of maximum 50%. Overall, the known process is rather expensive.

It is an object of the invention to provide an inexpensive, relatively simple and commercially attractive process for the preparation of enantiomerically enriched indoline-2-carboxylic acid according to formula (1) in acceptable yield.

This has been achieved according to the process of the present invention by subjecting to ring closure an enantiomerically enriched ortho-X-substituted phenylalanine compound according to formula (2),

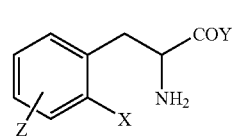

or salts thereof, in which Y and Z are as defined above and X is a leaving group, preferably at a temperature of below about 140° C. upon formation of enantiomerically enriched chiral optionally substituted indoline-2-carboxylic acid according to formula (1).

It has been surprisingly found that with the process of the present invention enantiomerically enriched indoline-2-carboxylic acid of formula (1) can be obtained in relatively high yield and enantiomeric excess (e.e). Moreover, the process of the invention is attractive for scaling up for industrial applications. Using the method of the invention greatly reduces the number of unit operations, necessary to obtain the indoline-2-carboxylic acid derivatives from readily available starting materials as compared to the prior art. Using the method of the invention is much more economic in the use of the starting materials, since in the processes known in the prior art half the final product was either discarded or needed to be upgraded by an expensive racemisation process. The process of the invention has the additional advantage that racemisation of the substrate (starting compound (2)) as well as of the reaction product (1) does not occur or occurs only to a limited extent.

The cyclisation process of the invention can be defined as an aryl amination reaction, which is generally known in the art as an Ulmann coupling reaction. The process relates to an intramolecular aryl amination reaction. The term "enantiomerically enriched" is equivalent to the term "optically active" and means that one of the enantiomers of a compound is present in excess compared to the other enantiomer. This excess will hereinafter be referred to as "enantiomeric excess" or e.e. (as for example determined by chiral GLC or HPLC analysis). The enantiomeric excess e.e. is equal to the difference between the amounts of enantiomers divided by the sum of the amounts of the enantiomers, which quotient can be expressed as a percentage after multiplication by 100. The term "indoline" is equal to "2,3-dihydro-1H-indole", the terms "ortho- or 2-X-substituted phenylalanine" are equal to "2-amino-3-(2-X-substituted phenyl)-propionic acid", the term "ortho- or 2-X-substituted cinnamic acid" is equal to "3-(2-X-substituted) acrylic acid" and these terms are used interchangeably throughout this application.

X in formula (2) is a leaving group and may be selected from the group consisting of a halogen atom chosen from fluoride, chloride, bromide, or iodide, a mesylate group, a nosylate, a tosylate group, a triflate group, boronic acid, or the like. X is preferably chosen from chloride, bromide, iodide, or a mesylate group, more preferably, X is chloride or bromide, even more preferred—because of it's low cost—is chloride.

Suitable examples of Z and Y in the enantiomerically enriched compounds according to formulae (1) and (2) are for example compounds in which Z is hydrogen, methyl, ethyl, isopropyl, trifluoromethyl, fluoride, hydroxyl, methoxy, ethoxy, benzyloxy, carboxylic acid, carboxylic acid methylester, nitril or combinations thereof and Y is hydroxy, methoxy, ethoxy, benzyloxy, amine, methylamine, dimethylamine, or benzylamine. The optional substitution in case of Z being a cyclic or acyclic aliphatic group, an aliphatic heterocyclic group, an (hetero)aryl group or an alkoxy group and in case of Y being an alkoxy or aryloxy group may be chosen from a trihalogenide, for example trifluoromethyl, trichloromethyl; a halogen atom, for example fluoride, chloride or iodide; an amine group, for example methylamine, dimethylamine, benzylamine, ethylamine, propylamine, phenylamine, 4-fluorophenylamine; an alkoxy or aryloxy group, for example, methoxy, ethoxy, isopropoxy, benzyloxy, phenoxy, 4-fluorophenoxy, 3-fluorophenoxy, 2-fluorophenoxy; a thioether, for example methyl thioether, ethyl thioether, benzyl thioether; an trihaloalkylether, for example trifluoromethylether; an aryl or heteroaryl, for example, phenyl, 4-fluorophenyl, 3-fluorophenyl, 2-fluorophenyl, 2-trifluoromethylphenyl, 3-trifluoromethylphenyl, 4-trifluoromethylphenyl, thiophene, furan, pyrazole, pyrole, imidazole, or the like. Preferred are compounds in which Z is hydrogen, trifluoromethyl, fluoride, hydroxy, methoxy or nitril and Y is hydroxyl. Preferably, Z in formula (1) is hydrogen and Y is hydroxyl, more preferred (S)-indoline-2-carboxylic acid is prepared with the process of the present invention. Suitable examples of salts of compounds according to formulae (1) and (2) are for example, the HCl salt, HBr salt, acetic acid salt, methane sulphonic acid salt, benzene sulphonic acid salt, the p-toluenesulphonic acid salt, maleic acid salt, tartaric acid salt, citric acid salt, or gluconic acid salt thereof.

Suitable examples of compounds according to formula (2) are for example 2-bromo-phenylalanine, 2-chlorophenylalanine, 2-iodo-phenylalanine, 2-bromo-phenylalanine methyl ester, 2-chlorophenylalanine methyl ester, 2-iodo-phenylalanine methyl ester, 2-bromophenylalanine ethyl ester, 2-chlorophenylalanine ethyl ester, 2-iodo-phenylalanine ethyl ester, 2-bromophenylalanine benzyl ester, 2-chlorophenylalanine benzyl ester, 2-iodo-phenylalanine benzyl ester, 2-bromophenylalanine amide, 2-chlorophenylalanine amide, 2-iodo-phenylalanine amide, or the like. Preferred are 2-bromophenylalanine, 2-chlorophenylalanine, 2-bromophenylalanine benzyl ester and 2-chlorophenylalanine benzyl ester. More preferred are 2-bromophenylalanine and 2-chlorophenylalanine. Even more preferred are the (S)-enantiomers of the respective examples of compounds (2).

In the process of the invention, the optical purity of the compound according to formula 2 (substrate) preferably is least about 50%, more preferred at least about 75%, even more preferred at least about 90%, particularly preferred at least about 95%, and most preferred at least about 98%.

Preferably, under the conditions of the cyclisation process of the present invention, the compound according to formula 2 may be converted into a compound according to formula 1 with a loss of stereochemical integrity of less than about 40%, more preferred less than about 20%, even more preferred less than about 10%, particularly preferred less than about 5%, and most preferred less than about 2%. Preferably, compound (2) is converted into compound (1) with substantially no loss in stereochemistry. The definition "loss of stereochemical integrity" equals the difference between the e.e. of compound (2) and the e.e. of compound (1) divided by the e.e. of compound (2), which quotient is expressed as a percentage after multiplication by 100.

Preferably, during the process of the invention, the stereochemistry of compound (2) is retained to such an extent that indoline-2-carboxylic acid of formula (1) can be obtained in an enantiomeric excess (e.e.) of at least about 30%, more preferred at least about 50% even more preferred at least about 80%, particularly preferred at least about 95% and most preferred at least about 98%.

The compound (1) may be enriched either in the optionally substituted (S)-indoline-2-carboxylic acid enantiomer or in the optionally substituted (R)-indoline-2-carboxylic acid enantiomer, preferably in the optionally substituted (S)-indoline-2-carboxylic acid enantiomer. Most preferred, (S)-indoline-2-carboxylic acid is prepared with the process of the present invention.

The process of the invention is applied at a temperature of below about 140° C., preferably between about 15 and about 130° C., more preferred between about 30 and about 120° C., particularly preferred between about 40 and about 110° C., most preferred between 60 and 100° C.

The addition of a metal catalyst is not a prerequisite for achieving acceptable yields and e.e.'s with the process of the present invention. Alternatively, the process of the invention may be efficiently applied in the presence of a relatively inexpensive metal catalyst or in the presence of a relatively small amount of a somewhat more expensive catalyst. Overall, the process of the present invention may be efficiently applied under reaction conditions that may yield a commercially attractive process at larger scale.

According to one embodiment of the present invention, the process may be carried out substantially in the absence of a metal catalyst. This has a particular advantage on the costs of the process and avoids the necessity of removing the catalyst after usage.

According to a further embodiment of the present invention, the process of the invention may be carried out in the presence of a metal catalyst, preferably a transition metal atom or ion. The metal atom or ion may act as a catalyst for the cyclization reaction of the invention and may be used as such or in combination with a ligand or coordinating group. Preferably, the metal is used as such, in the absence of a ligand. This is particularly preferred since it avoids the costs of—an often relatively expensive—ligand. The metal may be selected from the groups 8 to 11 of the Periodic Table of Elements, and may in particular be chosen from copper, gold, iron, ruthenium, cobalt, rhodium, iridium, nickel, palladium or platinum. Preferably, catalysts based on metals from groups 10 and 11 are used, more preferably metals chosen from copper, palladium, nickel, iron or ruthenium, or mixtures thereof, even more preferred copper, palladium or nickel, are used. Catalysts based on copper are particularly preferred since they are rather inexpensive and low amounts may be sufficient to yield products in good yields and e.e.

For example, when X in the compound of formula 2 is bromide, the process of the invention is preferably applied in the absence of copper or any other metal. When X is, for example, chloride, the process of the invention is preferably applied in the presence of a metal or a combination of metals selected from the list given above, more preferably in the presence of relatively small amounts.

The amount of metal catalyst used depends on the activity of the catalyst for the specific cyclization reaction and on the costs of the catalyst. A skilled person is able to choose the most economically feasible catalyst with respect to amount, type of metal, ligands and the like for the given conversion.

Preferably, the molar ratio between the metal atom or ion and the compound of formula (2) is between 0.00001 to 50 mol %, more preferred between 0.01 and 30 mol %, even more preferred between 0.05-15 mol %, particularly preferred between 0.1 and 7 mol %, even more preferred between 0.2 and 5 mol %, and most preferred between 0.5 and 3 mol %. When using the more expensive metals such as, for example, palladium, gold, ruthenium or rhodium, it is particularly preferred to use relatively small amounts, preferably between about 0.00001 and 7 mol %, more preferred between 0.01 and 5 mol %, even more preferred between 0.05-3 mol %, particularly preferred between 0.1 and 1 mol %, and most preferred between 0.2 and 0.5 mol %.

The use of none or low amounts of metal in the process of the invention has the advantage that metal removal is not required or is easier.

Suitable examples of metals that may be used in the process of the invention are any metals from the groups 8 to 11 of the Periodic table as indicated above which are known to a person skilled in the art of aryl amination reactions.

Examples of copper atoms or ions that can be used in the process of the present invention are copper metal or organic or inorganic compounds of copper(I) or copper(II). Suitable examples of copper catalysts in the process of the invention are copper(I)chloride, copper(II)chloride, copper(I)bromide, copper(II)bromide, copper(I)iodide, copper(II)iodide, basic copper(II)carbonate, copper(I)nitrate, copper(II)nitrate, copper(II)sulphate, copper(I)sulfide, copper(II)sulfide, copper(I) acetate, copper(II)acetate, copper(I)oxide, copper(II)oxide, copper(I)trifluoroacetate, copper(II)trifluoroacetate, copper (I) benzoate, copper(II) benzoate, copper(II)trifluoromethyl sulphonate, and the like. Preferred are copper(I)chloride, copper(II)chloride, copper(I)bromide and copper(II)bromide. These catalysts are readily available and relatively inexpensive. Suitable examples of gold atoms or ions can be chosen from for example gold metal, gold(I)chloride, gold(III)chloride, gold(III)oxide, and the like. Suitable examples of iron metals are iron(II)chloride, iron(III)chloride, iron(II)bromide, iron(III)bromide, iron(II)oxide, iron(III)oxide, and the like. Suitable examples of ruthenium metals are ruthenium (III)bromide, ruthenium(III)chloride, and the like. Examples of suitable cobalt metals are Raney Cobalt, cobalt(II)chloride, cobalt(II)bromide, cobalt(II)oxide, or the like. Examples of suitable rhodium metals are for example rhodium(II)acetate dimer and rhodium(III)chloride. Examples of suitable iridium metals are e.g. iridium(III)bromide and iridium(III)chloride. Examples of suitable nickel metals are e.g. nickel powder, nickel(II)bromide, nickel(II)chloride, or Raney nickel. Examples of suitable palladium metals are palladium(II)chloride, palladium(II)acetate, or the like. Examples of suitable platinum metals are platinum(II)bromide, platinum(II)chloride, platinum(IV)chloride and platinum(IV)oxide.

When the process of the invention is carried out in the presence of a metal, a ligand/coordinating group—even though not necessary—may be present. With the term "coordinating group" is meant that the group is capable of binding with a transition metal atom or ion, preferably by donating electron density to a transition metal atom or ion. The ligand may be chosen from a monodentate (i.e. comprising one coordinating atom or group that binds on the metal), bidentate (i.e. comprising two coordinating atoms or groups that bind on the metal, said two coordinating groups being linked together forming said bidentate ligand), tridentate, tetra- or polydentate ligand, or a combination of two or more thereof. The coordinating atoms may be chosen from the groups consisting of nitrogen, oxygen, phosphorus, and sulphur, preferably chosen from nitrogen, oxygen or sulphur since phosphorus containing ligands are usually relatively sensitive to oxidation and/or removal thereof from the reaction mixture may be more difficult. Examples of suitable ligands are known to the person skilled in the art and are for example disclosed in S. Ley, A. W. Thomas. *Angew. Chem. Int. Ed.* 2003, 42, 5400-5449. The ligand may also serve as a solvent in the process of the invention.

The ratio between the ligand and the metal atom may suitably be 0.1 or higher, preferably, between 1 and 10 and more preferred between 1 and 3.

The metal atom or ion and the ligand—if present—of the catalyst may be added to the reaction mixture separately or simultaneously, or they may be added in the form of a pre-formed catalyst complex. A suitable example of a preformed catalyst complex is Cu(II)(2,4-pentanedione)$_2$.

The process of the present invention is preferably carried out in the presence of a base. The base may be chosen from amines, bases and basic salts from alkali metals and earth alkali metals, and heterogeneous bases such as for example basic ion exchangers, basic zeolites, or the like. Amines may be chosen from primary amines, such as for example butylamine, hexylamine, heptylamine, octylamine, benzylamine, ethylenediamine, monoethanolamine, or the like; secondary amines such as for example diethylamine, dibutylamine, diethanolamine, morpholine, piperidine, pyridine and the like, or tertiary amines such as for example diisopropylethylamine, triethylamine, tripropylamine, tributylamine, 4-N,N-dimethylaminopyridine or the like. Suitable examples of basic ion exchangers may be Amberlite IRA 67, Dowex 1, Dowex 2, and the like. Suitable examples of basic zeolites may be for example CsNa—Y and the like as disclosed in *Chem. Rev.* 1995, Vol. 95, pages 537-558. The base is preferably chosen from bases and basic salts from alkali metals and earth alkali metals because of a generally easy work-up. More preferably the base is chosen from the group of alkali metal and earth alkali metal carbonates, and alkali metal and earth alkali metal hydrogen carbonates, alkali metal and earth alkali metal acetates, alkali metal and earth alkali metal hydroxides, alkali metal and earth alkali metal alkoxides, and alkali metal and earth alkali metal phosphates. Preferred alkali metals and earth alkali metals are Na, K, Ca and Mg. More preferred, the base is chosen from $K_2CO_3$, NaOAc, KOAc, $Na_2CO_3$, $CaCO_3$, $K_3PO_4$, $NaHCO_3$, $Li_2CO_3$, and $Cs_2CO_3$. Especially preferred bases are $K_2CO_3$, $Na_2CO_3$, $K_3PO_4$, NaOAc and KOAc, since these bases are readily available and inexpensive. Most preferred bases are $K_2CO_3$, $Na_2CO_3$ and $K_3PO_4$.

The process of the invention may be applied in a solvent, such as for example an organic solvent, water, ionic liquids as for example described in T. Welton, *Chem. Rev.*, 99, 2071-2083 (1999), or the like. Suitable solvents that can be used in the process according to the invention are solvents that do not react under the reaction conditions, for example polar solvents, such as for example ethers, amides and the like, or hydrocarbons, such as toluene. Also a mixture of solvents may be used. Particularly suitable solvents are aprotic polar solvents, for example, N-methyl pyrrolidinone (NMP), dimethyl formamide (DMF), dimethyl acetamide (DMA), dimethyl sulphoxide (DMSO), acetonitrile, glymes, for example ethyleneglycol dimethylether, and the like. N-methyl pyrrolidinone (NMP) is a particularly suitable solvent in the process of the present invention. Furthermore, NMP is an environmental friendly solvent. In specific cases reactants, bases, ligands and/or products can serve as a solvent.

According to one preferred embodiment of the present invention, the process is carried out in water. Advantages of the use of water are that water is an highly environmental friendly solvent, is cheap and is highly abundant. Moreover, a compound according to formula (1) can in general relatively easily be obtained from water or an aqueous environment, for example by adjusting the pH and subsequently, for example by filtration of said compound (1) or by extraction of said compound (1) into an organic phase. The use of water as solvent is particular advantageous if the starting compound of formula (2) is made via an enzymatic process in water as described further below under "Preparation process (A)", since in that case, no organic solvents are needed for the largest part of the manufacturing. In case the reaction is carried out in aqueous solution, the salt of the starting material of formula (2) can optionally itself serve as a base or can be used in combination with an externally added base as listed above.

The process according to the invention may be applied in the presence of one or more additives like, surfactants, such as phase-transfer catalysts, such as, for example quaternary ammonium salts, in particular tetrabutylammonium chloride or bromide, triethylbenzylammonium bromide, or tetraethylammonium chloride, salts, and the like. Other possible additives are salts, such as for example lithiumchloride. The process according to the invention may be applied by using external stimuli, for example by microwave heating, ultrasound or light.

The process of the present invention is generally carried out at atmospheric pressure or in a closed vessel. The process is preferably carried out in a nitrogen or argon atmosphere.

The order in which the reagents are added is not critical. One suitable order may be that in which the compound (2), the optional base, optionally the catalyst/metal, and optionally the solvent and/or water are charged. Then, the reaction mixture is heated to the desired temperature. Another suitable order may be that in which the optional solvent is charged and in which compound (2) and the optional components are added thereto. Another suitable order may be that in which a mixture of the solvent and compound (2) are charged and the other optional reagents are added thereto.

In case a catalyst is used, said catalyst may be separated from the reaction mixture by, for example, extraction, filtration, decanting or centrifuging or by addition of a complexing agent which may cause precipitation or dissolution of the metal. Suitable examples of complexing agents are, for example sulphur or nitrogen containing compounds, such as for example ethylene diamine tetraacetic acid (EDTA), diethylene triamine pentaacetic acid (DTPA), or immobilized forms thereof, and the like, ammonia, quinolins, bisquinolins and the like, natrium(II) sulfide, thiocyanuric acid and the like, acidic ion exchangers and the like. Further suitable ways to separate the catalyst from the reaction mixture may be by bioabsorption on an enzyme, by complexation with a zeolite, by adsorption on a solid carrier, such as celite or silica, or by any other method known to the person skilled in the art. In case a copper metal is used, preferably in relatively small amounts such as between about 0.00001 and 7 mol % relative to the amount of compound (2), the copper metal is preferably removed by extraction, filtration, filtration over a solid carrier or by complexing with, for example, EDTA or thiocyanuric acid.

The product (1) obtained with the process of the present invention may be further purified by methods commonly known in the art, for example, by extraction, crystallization, distillation or chromatography.

With the process of the present invention, the enantiomerically enriched indoline-2-carboxylic acid of formula (1) may be obtained with relatively high conversion and yield.

The yield obtained with the process of the present invention is preferably at least 30%, more preferred at least 40%, even more preferred at least 50%, particularly preferred at least 60% and most preferred at least 80%.

Compound (1), in particular optically active (S)-indoline-2-carboxylic acid, may be used as an intermediate in pharmaceutical products, in particular in the preparation of Perindopril, Pentopril or Indolapril.

Preparation of Compound (2)

The process of the present invention involves an enantiomerically enriched ortho-substituted phenylalanine compound according to formula (2) as defined above. This enantiomerically enriched compound (2) may be prepared according to several different processes, preferably according to the processes (A) to (G) and further suitable processes disclosed in the present application, preferably (A) to (D), more preferred (A) to (C), and most preferred process (A) or (B).

The following figure visualizes the specific conversion according to processes (A) and (B) as described below:

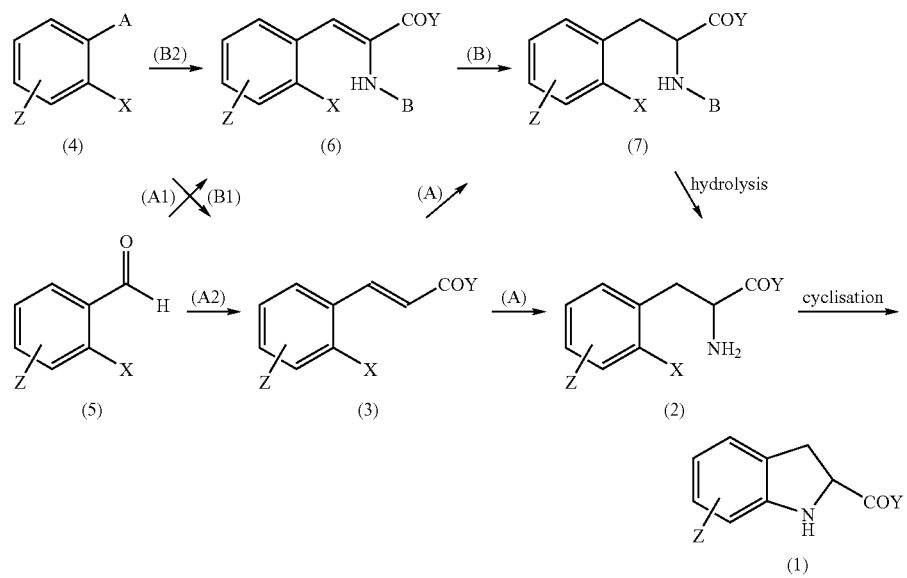

Preparation Process (A) to Form Enantiomerically Enriched Compound (2) [PAL-Step]

In one embodiment of the invention, the enantiomerically enriched compound (2) is prepared from the corresponding ortho-X-substituted cinnamic acid derivative of formula (3)

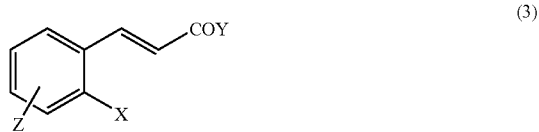

(3)

or a salt thereof, wherein X, Y and Z are as defined above by reacting the compound of formula (3) with an amino group donor in the presence of an stereoselective phenylalanine ammonia lyase enzyme (PAL). This embodiment will be referred to hereafter as PAL-step or Process (A).

Preferably, in this embodiment of the invention, the X in 2-X-substituted cinnamic acid of formula (3) stands for bromide or chloride, preferably chloride since particularly good results are obtained in case of X being chloride.

With 'stereoselectivity' of PAL is meant that PAL preferentially catalyses the formation of one of the enantiomers of the compound (2). The stereoselectivity of an enzyme may be expressed in terms of E-ratio, the ratio of the specificity constants $V_{max}/K_m$ of the two enantiomers as described in C-S. Chen, Y Fujimoto, G. Girdaukas, C. J. Sih., *J. Am. Chem. Soc.* 1982, 104, 7294-7299. In the framework of the invention, the E-ratio of a PAL is determined using the $V_{max}$ and $K_m$ values as determined in the non-oxidative deamination of the ortho-X-substituted phenylalanine compound (=compound (2)) using PAL.

Preferably, PAL forms products with an e.e. of >80%, more preferably, PAL forms products with an e.e. of >90%, even more preferably, PAL forms products with an e.e. of >95%, most preferably, PAL forms products with an e.e. of >99% Preferably, PAL stereoselectively catalyses the formation of the (S)-enantiomer of the compound (2), more preferably, in this embodiment of the invention, ortho-chloro-substituted (S)-phenylalanine compound (2) is formed.

In the framework of the invention, PAL is defined as an enzyme having the ability to catalyse the reversible non-reductive amination of ortho-X-substituted cinnamic acid derivative [compound (3)] to ortho-X-substituted phenylalanine compound (=compound (2)) and may be chosen from Phenylalanine ammonia lyases from the EC class 4.3.1, in particular from the EC class 4.3.1.5. Examples of suitable PAL enzymes are known to the person skilled in the art and include for example bacterial phenylalanine or tyrosine ammonia lyases, for instance from *Streptomyces maritimus* or *Rhodobacter capsulatus*, yeast phenylalanine ammonia lyases, for example PAL from *Rhodosporidium toruloides* (in literature sometimes also referred to as *Rhodotorula glutinis* or *Rhodotorula graminis* and plant phenylalanine ammonia lyases, for example PAL from *Petroselinum crispum* or *Zea mays*. Preferably PAL is chosen from the group of yeast phenylalanine ammonia lyases, more preferably from the group of PALs from *Rhodosporidium* sp. Even more preferred PAL is PAL from *Rhodosporidium toruloides*, in particular PAL from *Rhodosporidium toruloides* ATCC 10788. Most preferred, the PAL is *Rhodosporidium toruloides* PAL of which the protein sequence is the NCBI protein database sequence CAA31209

This embodiment of the invention is in no way limited by the form in which PAL is used. PAL may for example be present in the PAL-step in a form chosen from a crude enzyme solution, a purified enzyme solution, (permeabilized and/or immobilized) cells that naturally or through genetic modification possess PAL activity, in a lysate of cells with such activity, in immobilized form, in chemically modified form or further forms known to a person skilled in the art, or in a combination of two or more of these forms.

It will be clear to the person skilled in the art that use can also be made of mutants of naturally occurring (wild type) PAL enzymes. For example, it is possible to make PAL-activity mutants, i.e. mutants which show a higher activity than wild type PAL on at least one substrate, PAL-expression mutants, i.e. mutants which are better expressed than wild type PAL; and the like. PAL-activity-mutants of wild-type enzymes can for example be made by modifying the DNA encoding the wild type enzymes using mutagenesis techniques known to the person skilled in the art (random mutagenesis, site-directed mutagenesis, directed evolution, gene shuffling, etc.) so that the DNA encodes an enzyme that differs by at least one amino acid from the wild type enzyme and by expressing the thus modified DNA in a suitable (host) cell. Alternatively, PAL-expression mutants may be prepared by modifying the DNA encoding wild type PAL enzymes using mutagenesis techniques known to the person skilled in the art, such that if the DNA is expressed in a (host) cell, the level of expression of PAL is higher for the mutated DNA than for the non-mutated DNA. The skilled person knows how to select these PAL-expression mutants, for example by measuring the relative activity for at least three different substrates and by comparing the ratio of the activities with the wild type enzyme. Expression mutants have a higher activity for all the different substrates, while the ratio of the activities between the substrates is equal to that of the wild type enzyme. Mutants of the PAL enzyme may have improved properties with respect to (stereo)selectivity and/or activity and/or stability and/or solvent resistance and/or pH profile and/or temperature profile, and/or expression and/or product and/or substrate inhibition and said mutants of PAL may be specifically selected based on the presence of any of these improved properties alone or in combination of two or more thereof.

Suitable amino group donors include for example $NH_3$ or $NH_4OH$ or B—$NH_2$, wherein B is a —$COR^1$ group in which $R^1$ may be chosen from an optionally substituted cyclic or acyclic aliphatic group with 1-10 carbon atoms, an optionally substituted aliphatic heterocyclic group with 1-10 carbon atoms, an optionally substituted (hetero)aryl group, an optionally substituted alkoxy group with 1-10 carbon atoms, an optionally substituted sulfonyl group or the like. If the amino group donor is B—$NH_2$, the compound (7) as obtained will be subjected to an additional hydrolysis step upon which compound (2) is formed (as described for process (B) further below). Preferred are $NH_3$ and $NH_4OH$. It is of course also possible to use a combination of various amino group donors.

It may be of advantage to add a reducing agent to the PAL-step for reducing the negative effects of oxygen on the PAL life. Examples of such reducing agents include hydrogen sulfide, thioglycolic acid, thiosulfuric acid, nitrous acid, sulfurous acid, ammonium and metal salts of the above, dithiothreitol, ethylmercaptan, ethylenemercaptan, methylmercaptan, 2-mercaptoethanol, hydrogen, nitrous oxide, iron (II) compound, manganese (II) compounds, sulfur and zinc. Preferably, to reduce the effects of oxygen on the PAL life, the PAL-step may be performed under anaerobic conditions in a manner known to the person skilled under the art, for example, by performing the PAL-step under a nitrogen atmosphere. The person skilled in the art can perform routine experiments to choose the optimal reaction conditions with respect to—amongst others—temperature, pH, concentration, and solvents.

Preferably, the temperature of the PAL-step is chosen such that the activity of the chosen PAL is optimal. For example, the preferred reaction temperature for the PAL of *R. glutinis* lies in the range from 0 to 50° C., in particular from 25 to 45° C., most in particular from 27 to 37° C.

Preferably, the pH of the PAL step and the concentration of the amino group donor (preferably $NH_3$) are chosen as such that the activity of the chosen PAL and the stability of compounds (2) and (3) and the yields in which these compounds are obtained are optimal. For example, the pH for the PAL of *R. glutinis* lies preferably in the range from pH 8 to pH 14, in particular in the range from pH 10 to 12, more in particular in the range from pH 10.5 to 11.5.

For example, the ammonium hydroxide ($NH_4OH$) concentration in water for the PAL of *R. glutinis* is chosen between about 5 and about 25 vol. %, in particular from about 10 to 15 vol. %, most in particular from about 12 to 14 vol. %.

The PAL-step may for example be performed in aqueous ammonia, to which optionally a co-solvent, a solubilization agent or an additive may be added in order to enhance to solubilization of compound (3) or to enhance the PAL activity or stability. Examples of co-solvents include dimethylformamide, tetrahydrofuranacetonitrile, glutaraldehyde, glycerol, toluene, ethanol, acetone, ether and dimethylsulfoxide (DMSO). Examples of solubilization agents include Triton X100 (made by Aldrich Chemical Company, Inc., Milwaukee, Wis.), Tween-80 (made by Aldrich Chemical Company, Inc., Milwaukee, Wis.), polyethylene glycol (PEG). Examples of additives include glutamic acid, isoleucine, ethylene glycol and sorbitol.

Compound (2) as obtained in the PAL-step may be used directly in the next step or may be purified first. The compound (2) obtained in the PAL-step may be purified from the reaction mixture obtained in the PAL-step by using conventional methods known to the person skilled in the art. For example, the reaction mixture obtained in the PAL-step comprising the compound (2) may be filtered or centrifuged (to remove the undissolved particles, such as for instance the host cells expressing PAL). Further, the amino group donor may for example be evaporated after which compound (2) may be isolated, preferably by precipitation of (2).

The yield obtained with the PAL-step is preferably at least 30%, more preferred at least 40%, even more preferred at least 50%, in particular preferred at least 60%, more in particular preferred at least 80%, most in particular at least 90%.

In a preferred embodiment of process (A), ortho-chloro-substituted (S)-phenylalanine compound according to formula (2) (wherein X stands for Cl) is prepared by reacting the corresponding 2-chloro-substituted cinnamic acid compound of formula (3) (wherein X stands for Cl) in an aqueous solution of ammonium hydroxide, the ammonium hydroxide concentration in water being from about 12 to 14 vol. % in the presence of PAL from *Rhodosporidium toruloides*. Preferably in this embodiment of process (A), the temperature is between 25 to 45° C. and the pH ranges from pH 10.5 to 11.5.

Compound (3) may for example be prepared by contacting a compound according to formula (4)

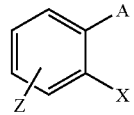

(4)

in which X and Z are as defined above and A is a leaving group, with an α,β-unsaturated compound, such as for example, acrylic acid, an acrylic ester or an acrylic amide in the presence of a transition metal catalyst comprising a transition metal and optionally a ligand [Process (A1)]. This process (A1) is preferably carried out by using a Heck reaction, such as for example disclosed in M. Larhed., A. Hallberg in *Handbook of Organopalladium Chemistry for Organic Synthesis* 2002, E. Negishi, Ed., Chapter IV. 2. In formula (4), A is a leaving group, which may be selected from F, Cl, Br, I, a triflate, a mesylate, a nosylate, a carbonyl chloride or sulfonyl chloride, an anhydride, an iodonium salt, a diazonium salt, boronic acid, and the like. Preferably, A in formula (4) is Cl, Br, I, more preferably Cl or Br.

Preferred compounds according to formula (4) are 1,2-dibromobenzene, 1-bromo-2-chlorobenzene, 1,2-dichlorobenzene, 1-bromo-2-iodobenzene, 1-chloro-2-iodobenzene, 2-bromo-benzenesulfonylchloride, 2-chlorobenzoylchloride, 2-chlorobenzoic anhydride and 2-chloro-benzenesulfonylchloride.

Preferred compounds according to formula (3) are 3-(2-bromo-phenyl)-acrylic acid, 3-(2-chloro-phenyl)-acrylic acid, 3-(2-bromo-phenyl)-acrylic acid methyl ester, 3-(2-chloro-phenyl)-acrylic acid methyl ester, 3-(2-bromo-phenyl)-acrylic acid benzyl ester and (2-chloro-phenyl)-acrylic acid benzyl ester.

The process (A1), preferably by applying a Heck reaction, is generally catalyzed by metal catalysts which may contain ligands. Suitable metals can be chosen from the group consisting of palladium, platinum, nickel, rhodium, ruthenium, cobalt, manganese or iron. Preferred metals are palladium or nickel, more preferred palladium. Suitable ligands are chosen from phosphines, bisphosphines, phosphonites, bisphosphonites, phosphites, bisphosphites, phosphoramidites, bisphosphoramidites, nitrogen containing ligands such as bipyridine, 1,10-phenanthroline or P, N-ligands which are defined as ligands that contain a phosphorus containing group and a nitrogen containing group. Palladacycles or palladium colloids may also be used. A suitable review describing many different catalysts for the Heck reaction is: Beletskaya, I. P.; Cheprakov, A. V.; *Chem. Rev.* 2000, 100, page 3009. The (A1) process (e.g. the Heck reaction) can also suitably be carried out without ligands and, even more suitable, with low loadings of palladium as disclosed by De Vries and coworkers in *Org. Lett.* 2003, Vol. 5, pages 3285-3288. The Heck reaction can be carried out in the presence of a base, such as $Et_3N$, NaOAc or the like, optionally in a dipolar nonprotic solvent such as NMP.

Compound (3) may further also be prepared by applying a condensation reaction to compound (5), such as for example an aldol condensation reaction, a Wittig reaction, a Perkin condensation reaction, a Knoevenagel condensation reaction or another process known to a person skilled in the art [Processes (A2)].

A suitable condensation process for preparing compound (3) is by reacting a compound according to formula (5)

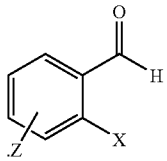

(5)

in which X and Z are as defined above, with an anhydride, for example acetic acid anhydride in the presence of a base [Process (A2)]. Preferably, the salt of the acid corresponding to said anhydride is used as the base. This process is known as the so-called Perkin reaction as disclosed in *March Advanced Organic Chemistry*, 5th Edition, Wiley Interscience, Eds, J. M. Smith and J. March, 2001, page 1229.

Another condensation method for preparing compound (3) is by contacting a compound according to formula (5) with a malonic acid derivative and a base, for example an amine in the so-called Knoevenagel condensation reaction as, for example, disclosed in *March Advanced Organic Chemistry*, 5th Edition, Wiley Interscience, Eds, J. M. Smith and J. March, 2001, page 1225.

Yet another method consists of the condensation of a compound of formula (5) with acetaldehyde in the presence of a base or in the presence of an enzyme, such as, for example, an aldolase, followed by oxidation with for instance oxygen.

Preferred compounds according to formula (5) are 2-bromobenzaldehyde or 2-chlorobenzaldehyde.

Preparation Process (B) to Form Enantiomerically Enriched Compound (2)

According to a further embodiment of the present invention, compound (2) may be prepared by contacting a compound according to formula (6)

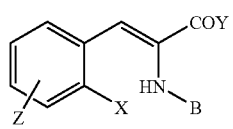

(6)

or a salt thereof, in which X, Y and Z are as defined above and B is a —COR$^1$ group in which R$^1$ may be an optionally substituted cyclic or acyclic aliphatic group with 1-10 carbon atoms, an optionally substituted aliphatic heterocyclic group with 1-10 carbon atoms, an optionally substituted (hetero) aryl group, an optionally substituted alkoxy group with 1-10 carbon atoms, an optionally substituted sulfonyl group or the like, with a hydrogen donor in the presence of a chiral catalyst comprising a transition metal upon formation of a compound according to formula (7)

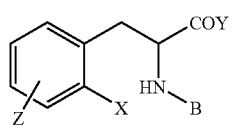

(7)

or a salt thereof, in which X, Y, Z and B are as defined above, and subjecting said compound (7) to an hydrolysis reaction upon formation of a compound according to formula (2) [Process (B)].

Suitable examples of B in formulae (6) and (7) are formyl, acetyl, chloroacetyl, trifluoroacetyl, phenylacetyl, benzoyl, methylsulfonyl, trifluorosulfonyl, benzenesulfonyl, toluenesulfonyl, t-butoxycarbonyl, benzyloxycarbonyl, or the like. Preferred are formyl, acetyl, trifluoroacetyl, benzoyl, toluenesulfonyl, and t-butoxycarbonyl, and more preferably B is acetyl or benzoyl.

Suitable compounds of formula (6) are for example 2-acetylamino-3-(2-chlorophenyl)-acrylic acid, 2-acetylamino-3-(2-chlorophenyl)-acrylic acid methyl ester, 2-acetylamino-3-(2-bromophenyl)-acrylic acid, 2-acetylamino-3-(2-bromophenyl)-acrylic acid methyl ester, 2-benzoylamino 3-(2-chlorophenyl)-acrylic acid, 2-benzoylamino 3-(2-chlorophenyl)-acrylic acid methyl ester, 2-benzoylamino 3-(2-bromophenyl)-acrylic acid, 2-benzoylamino 3-(2-bromophenyl)-acrylic acid methylester, and the like. Preferred are 2-acetylamino-3-(2-chlorophenyl)-acrylic acid and 2-acetylamino-3-(2-bromophenyl)-acrylic acid.

Suitable compounds according to formula (7) are 2-acetylamino-3-(2-bromo-phenyl)-propionic acid, 2-acetylamino-3-(2-chloro-phenyl)-propionic acid, 2-benzoylamino-3-(2-bromo-phenyl)-propionic acid, 2-benzoylamino-3-(2-chloro-phenyl)-propionic acid, 2-acetylamino-3-(2-bromo-phenyl)-propionic acid methyl ester, 2-acetylamino-3-(2-chloro-phenyl)-propionic acid methyl ester, 2-acetylamino-3-(2-bromo-phenyl)-propionic acid benzyl ester, and 2-acetylamino-3-(2-chloro-phenyl)-propionic acid benzylester. Preferred compounds according to formula (7) are 2-acetylamino-3-(2-bromo-phenyl)-propionic acid and 2-acetylamino-3-(2-chloro-phenyl)-propionic acid.

The part of this process in which compound (7) is prepared is known as an asymmetric (transfer) hydrogenation process, wherein an enantiomerically enriched compound (7) is prepared by using a chiral transition metal catalyst comprising at least an enantiomerically enriched ligand to ensure that the double bond of a prochiral compound (compound (6) in this particular process) is asymmetrically reduced through hydrogen transfer with a hydrogen-donating organic compound (hereby defined as the hydrogen donor).

Suitable chiral catalysts for asymmetric (transfer) hydrogenation comprise a transition metal complex compound of an enantiomerically enriched chiral ligand L, optionally a counterion and optionally a further ligand S, the latter being either chiral or non-chiral.

Transition metals which can be suitably used in the asymmetric transfer hydrogenation process of the present invention are metals chosen from groups 8, 9 and 10 of the Periodic Table of Elements, such as for example, palladium, ruthenium, rhodium and iridium, most preferred are ruthenium, and rhodium.

Chiral ligands L, which can be used are, bidentates, for example, enantiomerically enriched bisphosphines, for example DIOP, BINAP, CHIRAPHOS, BICP, DIPAMP, SKEWPHOS, TANIAPHOS, JOSIPHOS, BPPM and the like, enantiomerially enriched bisphosphinites, for example spirOP, BICPO and the like, biphosphonites and bisphosphites, all of which are disclosed in Noyori et al. in *Catalytic Asymmetric Synthesis*, Ed I. Ojima, Chapter 1, which is incorporated herein by reference.

Alternatively, monodentate ligands can be used, for example, phosphoramidites as disclosed in WO 02/04466, the preparation and use thereof being incorporated herein by reference, phosphites and phosphonites as disclosed in T.

Jerphagnon, J. L. Renaud and C. Bruneau, *Tetrahedron: Asymmetry*, 2004, Vol. 15, pages 2101-2111, in De Vries et al., *Adv. Synth. Catal.* 2003, Vol. 345, pages 308-323 and in Blaser et al. *Adv. Synth. Catal.* 2003, Vol. 345, pages 103-151. In case mondentate ligands are used it is possible to use a mixture of two different chiral enantioenriched monodentate ligands. It is also possible to use a mixture of a chiral mondentate ligand and a non-chiral ligand such as triphenylphosphine. It is also possible to use other ligands that contain two nitrogen atoms or a nitrogen and a phosphorus atom as donating atoms (see for instance A. Pfaltz et al in *Adv. Synth, Catal.*, 2003, Vol. 345, pages 33-43.

The diol part and/or the amine part of the chiral monodentate ligand can be enantiomerically enriched in the case of phosphoramidites, the diol part and/or the alcohol part can be enantiomerically enriched in the case of phosphites, the diol part and/or the hydrocarbon part can be enantiomerically enriched in the case of phosphonites. Obviously, one enantiomer of the ligand will give compound (7) with a certain configuration (R or S), whereas the opposite enantiomer of the ligand can give compound (7) with the opposite configuration (S or R). Preferably, a chiral catalyst is used that is capable of preferentially converting compound (6) into the (S)-enantiomer of compound (7). Additionally, the metal itself can be optically active as well.

Use is preferably made of enantiomerically enriched chiral monodentate ligands L having the formula (I),

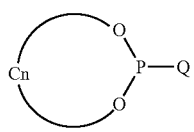
(I)

where $C_n$ together with the two O-atoms and the P-atom forms a substituted or non-substituted ring with 2-6 C-atoms, Q stands for OR or $NR^1R^2$; wherein R, R1 and $R^2$ each independently stand for hydrogen, an optionally substituted alkyl, aryl, aralkyl or alkaryl group, or may form an optionally heterocyclic ring together with the N-atom to which they are bound.

In the chiral ligand L of formula (I) $C_n$ and/or R, $R^1$ and/or $R^2$ are chiral or are part of a chiral entity. $C_n$ preferably represents a chiral substituted $C_4$ chain (chain with 4 optionally substituted C-atoms), of predominantly one configuration, for example with an enantiomeric excess larger than 95%, in particular larger than 99%, more in particular larger than 99.5%. Preferably $C_n$ together with the two O-atoms and the P-atom forms a 7-membered ring with 4 C-atoms which 2 by 2 form part of an aryl group or a naphthyl group.

Preferably, the enantioselectivity (e.e.) of the chiral catalyst used for the asymmetric hydrogenation process (B) to convert compound (6) into compound (7) is at least 85%, more preferred at least 90%, even more preferred at least 95%, particularly preferred at least 98% and most preferred at least 99%.

Examples of suitable chiral monodentate ligands of formula (I) are disclosed in WO 02/04466 and WO 01/94278 which examples are incorporated herein by reference.

As a solvent use can be made of: alcohols, esters, amides, ethers, aromatic hydrocarbons, halogenated hydrocarbons, or the like. Preferred are ethyl acetate, isopropylacetate, methyl-t-butylether, tetrahydrofuran, toluene, acetone, methylisobutylketone and dichloromethane, most preferred are ethylacetate and dichloromethane. It is also possible to carry out the asymmetric (transfer) hydrogenation in ionic liquids as described in T. Welton, *Chem. Rev.*, 1999, 99, 2071-2083, so that isolation of the product is simplified. If necessary, the solubility of the ligand in the ionic liquid can be increased by providing the ligand with polar groups such as carboxylate salts.

When using phosphoramidites as ligand (when Q in formula (I)=$NR^1R^2$), the asymmetric hydrogenation process may optionally be accelerated by increasing the pressure. The pressure can be between 1 and 100 bar, more preferred between 2 to 80 bar, and most preferred from 3 to 60 bar.

The temperature at which the asymmetric (transfer) hydrogenation is carried out is generally a compromise between reaction velocity and enantioselectivity, and preferably lies between −20 and 120° C., in particular between 0 and 60° C. The asymmetric (transfer) hydrogenation is preferably carried out with oxygen being excluded. Preferably the substrates and solvents do not contain any oxygen, peroxides or other oxidizing substances.

In the asymmetric transfer hydrogenation process (Process (B)) of the invention the prochiral double bond of compound (6) is asymmetrically reduced through hydrogen transfer in the presence of one or more hydrogen donors, which in the context of this invention are understood to be compounds that can in some way transfer hydrogen to the substrate. Suitable hydrogen donors that can be used are preferably $H_2$—in which case the process is defined as an asymmetric hydrogenation process but may also be aliphatic or aromatic alcohols with 1-10 C-atoms, in particular secondary alcohols with 1-10 C-atoms, for example isopropanol or cyclohexanol, or unsaturated hydrocarbons with 5-10 C-atoms, for example 1,4-dihydrobenzene or hydroquinone, reducing sugars, for example glucose or derivates of formic acid, for example ammonium formate or an azeotropic mixture of formic acid and triethylamine. Preferably, formic acid, isopropanol or cyclohexadiene are used.

The molar ratio of substrate (compound (6)) to hydrogen donor preferably lies between 1:1 and 1:100. The hydrogen pressure may vary within wide limits and is preferably chosen to be as high as possible when a fast reaction or the lowest possible amount of catalyst is desired. The hydrogen pressure for example lies between 0.05 and 20 MPa, preferably between 0.1 and 10 MPa, in particular between 0.15 and 8 MPa.

In the asymmetric hydrogenation of compound (6) use is preferably made of a molar ratio of metal present in the transition metal compound to compound (6), the substrate, of between 1:10 and 1:1,000,000, in particular between 1:50 and 1:100,000.

The yield obtained with the asymmetric hydrogenation process converting compound (6) to compound (7) is preferably at least 50%, more preferred at least 70%, even more preferred at least 80%, particularly preferred at least 90% and most preferred at least 95%.

Preferably, during the asymmetric hydrogenation process of the invention, compound (7) can be obtained in an enantiomeric purity (e.e.) of at least about 50%, more preferred at least about 75% even more preferred at least about 85%, particularly preferred at least about 95% and most preferred at least about 98%.

According to this particular preparation process (B), compound (7) may be subjected to an hydrolysis reaction, for example by contacting compound (7) with an acid, for example by treatment with HCl, $H_2SO_4$, acetic acid or p-toluenesulphonic acid, or by contacting compound (7) with a base, for example NaOH, $Na_2CO_3$ or $K_2CO_3$ or by treatment of compound (7) with an enzyme, for example with an acylase or the like to give a compound according to formula (2). Conversions from compound (7) to compound (2) can be done in a manner known to the person skilled in the art, for example as disclosed in *J. Am. Chem. Soc.* 1988, Vol. 110, pages 6162-6172 and in *J. Org. Chem.* 1990, Vol. 55, pages 6000-6017, and in *J. Org. Chem.* 1984, Vol. 49, pages 2819-2820.

As solvents for the hydrolysis reaction, organic solvents or water may be used, for example alcohols or esters. Preferred is water because the next step, the conversion of compound (2) to compound (1), can also be carried in the same solvent, which solvent is in particular environmentally friendly and inexpensive.

The compound according to formula (6) may be prepared by contacting a compound according to formula (5) with an N-functionalized glycine derivative having formula B—NH—CH$_2$—COY wherein Y is as defined above and converting an optionally intermediately formed azlactone compound to the compound of formula (6) [Process (B1)]:

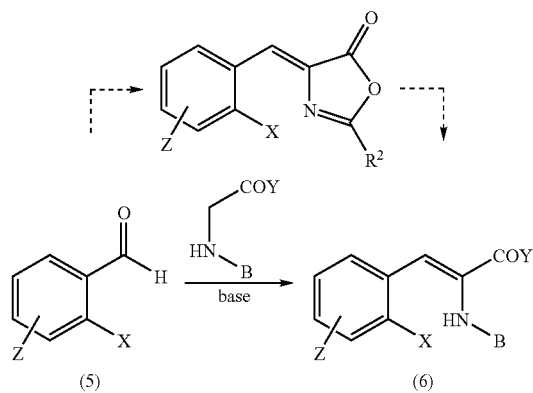

Preferred N-functionalized glycine derivatives are N-functionalized glycine acid, N-functionalized glycine ester, and N-functionalized glycine amide.

Typical processes (B1) to convert compound (5) into compound (6) are known to a person skilled in the art and are for example described in Laneman et al. in Chem. Ind. 1998, 75 and in Jendrella et al. *Tetrahedron* 1995, Vol. 51, pages 12047-12068, which are both incorporated herein by reference. This process can for example be applied by reacting a compound of formula (5) with said N-functionalized glycine derivative in the presence of sodium acetate and acetic acid anhydride. The hydrolysis of the intermediate azlactone compound, when formed, can be done with an acid or a base, for example by using acetic acid in water or by a metal hydroxide such as for example sodium hydroxide in water.

A compound according to formula (6) can also be prepared by reacting a compound according to formula (4) with a functionalized acrylate derivative, preferably an acrylic enamide derivative such as, for example, an acrylic acid enamide, an acrylic ester enamide or an acrylic amide enamide [Process (B2)]. Preferably, a Heck reaction can be applied, such as for example disclosed by Willans, de Vries et al. in *J. Organomet. Chem.* 2003, Vol. 687, pages 494-497:

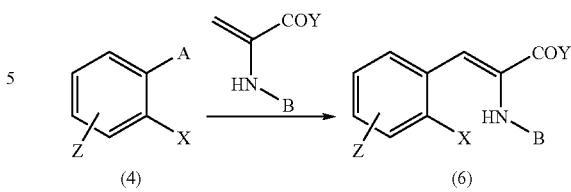

The reaction is generally carried out as described above for the Heck reaction. Preferably, the reaction is carried out in the presence of a transition metal catalyst. Optionally the reaction may be carried out in the presence of a base, optionally in a solvent, preferably an organic solvent. A suitable acryl ester enamide may be N-acetyl glycine methyl ester, which can be contacted with for example 2-chloro bromobenzene in the presence of, for example Pd(OAc)$_2$ and optionally a base, such as for example sodium acetate or diisopropyl ethylamine, for example in NMP as solvent to give 2-acetylamino-3-(2-chlorophenyl)-acrylic acid methyl ester according to formula (6).

Preparation Processes (C) to Form Enantiomerically Enriched Compound (2)

A further suitable way to prepare compound (2) is by using a classical resolution process [Process (C1)]. Such a process comprises reacting a reaction mixture comprising both enantiomers of the compound according to formula (2) with a suitable resolution agent. For example, in the case when Y is H, a substituted or non-substituted alkoxy group with 1-10 carbon atoms or a substituted or non-substituted aryloxy group, the reaction mixture may be contacted with an acidic resolving agent, such as for example tartaric acid, mandelic acid or camphor sulphonic acid upon formation of a diastereomeric salt of one of the enantiomers of compound (2) with said resolution agent. This may be done by methods as for example disclosed in "Stereochemistry of Organic Compounds" Wiley Interscience, Eds. Eliel E., Wilen S. H., 1994, Chapter 7. The formed diastereomers may be separated via crystallization and the required enantiomerically enriched compound (2) may be isolated after separation from the diastereomeric salt.

Alternatively, a classical resolution process said racemic mixture of the enantiomers of compound (2) or compound (7) respectively in which Y is hydroxyl and B is as defined above may be applied by using a basic resolving agent, such as for example ephedrine, α-phenylethylamine, or quinine, as for example disclosed by L. R. Overby and A. W. Ingersoll, *J. Am. Chem. Soc.* 1960, Vol. 81, pages 2067-2069. The formed diastereomers may be separated via crystallization and the required enantiomerically enriched compound (2) or compound (7) may be isolated after separation from the diastereomeric salt. In case of resolution of compound (7), either by an acidic or basic resolving agent, the obtained enantiomerically enriched compound (7) is subsequently subjected to an hydrolysis reaction as described above to give compound (2).

The racemic mixture of both enantiomers of compound (2) or (7) may be prepared according to any of the methods (B) above, when carried out non-stereoselectively.

The racemic mixture of compound (2) can also be prepared by condensation of a compound according to formula (5) with an hydantoin, followed by hydrogenation of the formed intermediate benzylidene compound and hydrolysis of the obtained hydantoin by chemical or enzymatic methods known by a person skilled in the art, for example as disclosed by S. G. Burton and coworker in *Tetrahedron Asymmetry*, 2004, vol. 15, pages 2737-2741 [Process (C2)].

Preparation Processes (D) to Form Enantiomerically Enriched Compound (2)

A further suitable way for preparing an enantiomerically enriched compound (2) is by applying an enzymatic resolution process on a reaction mixture comprising both enantiomers of compound (7) [Process (D)]. For example by enzymatic hydrolysis of the N—B bond in one of the enantiomers of a compound of formula (7) by using, for example an acylase, whereupon a mixture of one enantiomer of compound (2) and the opposite enantiomer of compound (7) is formed, followed by separation of said one enantiomer of compound (2) from said mixture. Another method is by enzymatic hydrolysis of the C—Y bond of compound (2) or (7) in the case Y is $NH_2$ by using, for example an amidase [Process (D1)]. Another method is by enzymatic hydrolysis of the C—Y bond of compound (2) or (7) in the case Y is $NH_2$ by using, for example an amidase [Process (D1)].

A further suitable way is by enzymatic hydrolysis of the C—Y bond of compounds (2) and/or (7), in the case when Y is a substituted or non-substituted alkoxy group with 1-10 carbons atoms or a substituted or non-substituted aryloxy group, by using, for example, a lipase as disclosed by Roper and coworkers, *Synthesis* 1983, page 1041 [Process (D2)].

A further suitable way is by contacting a mixture comprising both enantiomers of respectively compound (2) or compound (7) with a PAL enzyme to convert one of the enantiomers of compounds (2) or (7) to a compound of formula (3), and separating the other enantiomer of compound (2), respectively (7), from said compound (3). [Process (D3)]

A further suitable way is by contacting a mixture comprising both enantiomers of respectively compound (2) or (7) with an aminotransferase to convert one of the enantiomers to a compound of formula (9) and obtain enantiomerically enriched compounds (2) or (7) [Process (D4)].

In case an enantiomerically enriched compound (7) is obtained according to process (D), said compound (7) may be subsequently subjected to an hydrolysis reaction as described above to give compound (2).

Further Preparation Processes (E)-(G) to Form Enantiomerically Enriched Compound (2)

A further suitable way to prepare compound (2) is by enzymatic hydrolysis of a hydantoin of formula (8) by using a hydantoinase enzyme [Process (E)]:

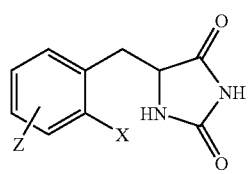

(8)

A further suitable way to prepare compound (2) is by applying enzymatic reductive amination, i.e. by contacting an α-keto acid, α-keto ester or α-keto amide of formula (9) or a salt thereof with, for example ammonia in the presence of an enzyme [Process (F)]:

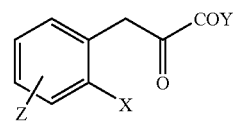

(9)

A further suitable way to prepare compound (2) is by using an aminotransferase, i.e. by contacting an α-keto acid, α-keto ester or α-keto amide of formula (9) with an aminodonor, for example glutamate or alanine in the presence of an aminotransferase enzyme [Process (G)].

Other suitable processes to prepare compound (2) are known to a person skilled in the art, for example as disclosed in *Chemistry of the Amino Acids*, Eds Greenstein J. P. Winitz M. Vol. 3, Krieger Publishing Company Inc., 1984, chapter 34.

Preferably, the process steps to prepare compound (1) are carried out without isolation or purification of the intermediate compounds (2-9).

The invention will be elucidated on the basis of the examples, without however being limited by them.

EXAMPLES

Definitions $C_{end}$ number of moles of product (1) formed at the end of the reaction.

$D_0$=number of moles of substrate (2) at the start of the reaction.

$D_e$=number of moles of substrate (2) at the end of the reaction.

The yield (%) may be defined by formula (4):

Yield (%)=$C_{end}/D_0$*100 (4)

The conversion (%) may be defined by formula (5):

Conversion (%)=$(D_0-D_e)/D_0$*100 (5)

The selectivity may be defined by formula (6):

Selectivity (%)=(yield/conversion)*100 (6)

Example 1

(S)-2,3-dihydro-1H-indole-2-carboxylic Acid: Conversion of (S)-2-bromophenylalanine with 2 mol % CuCl in NMP at 100° C.

A flask was charged successively with 366 mg (1.5 mmol) (S)-2-bromophenylalanine, 217 mg (1.6 mmol) $K_2CO_3$, 3.2 mg (0.03 mmol) CuCl and 3.2 g NMP. The reactor was flushed with argon and then kept under a slow stream of argon. The reaction mixture was stirred and heated until 100° C. and kept at this temperature. Samples were taken regularly and analyzed by HPLC. After 4 hours, full conversion of (S)-2-bromophenylalanine was found. The yield (measured in solution) of (S)-2,3-dihydro-1H-indole-2-carboxylic acid was 95.9%, ee>98.6%.

Example 2

(S)-2,3-dihydro-1H-indole-2-carboxylic Acid: Conversion of (S)-2-bromophenylalanine with 1 mol % CuCl in NMP at 80° C.

A flask was charged successively with 9.76 g (40.0 mmol) (S)-2-bromophenylalanine, 5.80 g (42.0 mmol) $K_2CO_3$, 40 mg (0.4 mmol) CuCl and 40 g NMP. The reactor was flushed with argon and then kept under a slow stream of argon. The reaction mixture was stirred and heated until 80° C. and kept at this temperature. Samples were taken regularly and analyzed by HPLC. After 3.5 h full conversion of (S)-2-bromophenylalanine was found. The reaction mixture was cooled to 25° C. and then 40 mL $H_2O$ and 50 mL aqueous EtOAc were added. The pH of this mixture was adjusted to 3.3 with 3.5 g 37% aqueous HCl. The phases were separated. The $H_2O$ phase was extracted with 2×50 mL aqueous EtOAc. The combined organic layers were washed with 25 mL sat aqueous NaCl. Then the organic phase was concentrated. The residue was dissolved in 16 mL 5N HCl, followed by pH adjustment to 2.1 with 9.4 g 32% aqueous NaOH. The precipitated (S)-2,3-dihydro-1H-indole-2-carboxylic acid was isolated by filtration and washed with 2×10 mL $H_2O$. 3.24 g (19.8 mmol) (S)-2,3-dihydro-1H-indole-2-carboxylic acid was found after drying. Yield 49.5%, ee>99%.

Example 3

(S)-2,3-dihydro-1H-indole-2-carboxylic Acid: Conversion of (S)-2-bromophenylalanine with 2 mol % CuCl in Water at 95° C.

A flask was charged successively with 366 mg (1.5 mmol) (S)-2-bromophenylalanine, 217 mg (1.6 mmol) $K_2CO_3$, 3 mg (0.03 mmol) CuCl and 3.4 g $H_2O$. The reactor was flushed with argon and then kept under a slow stream of argon. The reaction mixture was stirred and heated until 95° C. and kept at this temperature. Samples were taken regularly and analyzed by HPLC. After 2 hour full conversion of (S)-2-bromophenylalanine was found. The reaction mixture was cooled to 25° C. and analyzed by HPLC. The yield in solution of (S)-2,3-dihydro-1H-indole-2-carboxylic acid was 81.1%, ee>99%.

Example 4

(S)-2,3-dihydro-1H-indole-2-carboxylic Acid: Conversion of (S)-2-bromophenylalanine with 0.01 mol % CuCl in Water at 95° C.

A flask was charged successively with 4.89 g (20.0 mmol) (S)-2-bromophenylalanine, 2.93 g (21.2 mmol) $K_2CO_3$, 0.2 mg CuCl (2.9 mmol) and 39.7 g $H_2O$. The reactor was flushed with argon and then kept under a slow stream of argon. The reaction mixture was stirred and heated until 95° C. and kept at this temperature. Samples were taken regularly and analyzed by HPLC. After 4 h hour full conversion of (S)-2-bromophenylalanine was found. The reaction mixture was cooled to 25° C. Then the reaction mixture was acidified with 4.47 g 5M aqueous HCl until pH=4.4. The precipitated (S)-2,3-dihydro-1H-indole-2-carboxylic acid was isolated by filtration and washed with 2×10 mL $H_2O$. Found after drying 2.24 g (13.7 mmol) (S)-2,3-dihydro-1H-indole-2-carboxylic acid. Yield 69%, ee>99%.

Example 5

(S)-2,3-dihydro-1H-indole-2-carboxylic Acid: Conversion of (S)-2-bromophenylalanine without CuCl in Water at 95° C.

A flask was charged successively with 366 mg (1.5 mmol) (S)-2-bromophenylalanine, 217 mg (1.6 mmmol) $K_2CO_3$ and 3 g $H_2O$. The reactor was flushed with argon and then kept under a slow stream of argon. The reaction mixture was stirred and heated until 95° C. and kept at this temperature. Samples were taken regularly and analyzed by HPLC. After 5 h hour the conversion was approximately 37%. After 22 h full conversion of (S)-2-bromophenylalanine was found. The reaction mixture was cooled to 25° C. and analyzed by HPLC. The yield in solution of (S)-2,3-dihydro-1H-indole-2-carboxylic acid was 95.6%, ee>99%.

Example 6

Step (i) Preparation of 3-(2-chloro-phenyl)-acrylic Acid (Compound (3))

A mixture of 18.4 g (0.19 mol) of potassium acetate in 70.3 g (0.5 mol) 2-chlorobenzaldehyde is heated to 145° C. Next 76.5 g (0.75 mol) of acetic anhydride is added in 1 hour. After dosing of 0.50 mol of acetic anhydride the mixture became clear. The mixture is stirred at 145° C. during 18 hours. The hot reaction mixture is poured into a mixture of 670 g of 6.4 w/w % aqueous NaOH (1.1 mol, 2.1 eq based on 2-chlorobenzaldehyde) and 200 mL toluene at 80° C. The final pH was 7.4. After separation of the organic phase, the water layer is again extracted with 100 mL of toluene at 80° C. The combined water phases are acidified with 380 g of 25 w/w % $H_2SO_4$ to pH 4.6. Crystallization starts at pH 6.4. The mixture is cooled to 25° C. and the product is isolated by filtration, washed with 100 mL of water and dried (vacuo, 50° C.). 3-(2-chloro-phenyl)-acrylic acid was obtained as an off white solid (100.2 g, 0.55 mol, yield 55%).

Step (ii): Preparation of (S)-2-amino-3-(2-chloro-phenyl)-propionic Acid

The PAL gene of *R. glutinis* was synthesized by Genscript Corporation, Scotch Plains, USA according to the protein sequence of the PAL of *Rhodosporidium toruloides* ATCC 10788 which sequence is listed in the protein database of the NCBI under number CAA31209. The codons of the synthetic PAL gene were optimised for expression in *E. coli*. The synthesized gene was ligated in the SmaI site of pUC57 by Genscript to give the pUC57_PAL construct. The lyophilized plasmid (5 μg) (obtained from Genscript) was dissolved in 50 μl MilliQ water and 1 μl of this solution was used to transform an aliquot of *E. coli* DH5α chemically competent cells (Invitrogen, Breda, The Netherlands) according to the protocol of the supplier. After overnight growth on solid LB medium (10 g/l Bacto Trypton (Difco, Becton, Dickinson and Company, Sparks, Md., USA), 5 g/l Bacto Yeast Extract (Difco) and 5 g/l sodium chloride (Merck, Darmstadt, Germany) supplemented with 100 μg/ml Carbenicillin (Sigma, St. Louis, Mo., USA), at 37° C., one colony was transferred to 20 ml liquid LB medium containing 100 μg/ml carbenicillin. Glycerol stocks (8% final concentration glycerol) of this culture were prepared and stored at −80° C.

*E. coli* DH5α containing the pUC57_PAL construct as obtained above was inoculated in 1000 ml LB medium supplemented with 100 μg/ml Carbenicillin and grown overnight at 28° C. This culture was used to inoculate 10 liter TB medium (12 g/l Bacto Trypton, 24 g/l Bacto Yeast Extract, 2.31 g/l KH$_2$PO$_4$ (Merck), 12.54 g/l K$_2$HPO$_4$ (Merck), and 4 g/l glycerol (Sigma), pH 7.0, supplemented with 0.1 g/l Carbenicillin and IPTG (1 mM final concentration). The cells were fermented for 9.5 hours at 37° C. at a stirrer speed of 500 to 1500 rpm. The cells were harvested by centrifugation. A total yield of 230 gram of cells was obtained. These cells were stored as aliquots of 10 gram at −20° C.

Prior to the experiment, the appropriate amount of cells was thawed in cold water and resuspended in a suitable reaction solution.

1.8 g (10 mmol) 3-(2-chloro-phenyl)-acrylic acid was dissolved in 0.5 L 13 vol % of aqueous NH$_3$ and the pH adjusted to 11 with 25 w/w % aqueous H$_2$SO$_4$ (substrate solution). Then 130 g (wet weight) of *E. coli* cells containing the Phenylalanine Ammonia Lyase gene of *R. glutinis* (*E. coli* DH5α containing plasmid pUC57_PAL) were resuspended in 0.2 L 13 vol % aqueous ammonia (pH adjusted to 11 with 25 w/w % aqueous H$_2$SO$_4$). The cell suspension was added to the substrate solution and the volume adjusted to 1 L with 13 vol % aqueous ammonia. The reaction was stirred with 200 rpm at 30° C. in a closed vessel. During the first 1 h, every 5 minutes 0.91 g (5.0 mmol) of 3-(2-chloro-phenyl)-acrylic acid was added to the reaction medium. Then the feeding was continued with the addition of 0.91 g (5 mmol) 3-(2-chloro-phenyl)-acrylic acid every 25 minutes for another 7 h. After a total reaction time of 8.5 h, the cells were removed by centrifugation.

The yield of the reaction (determined using HPLC) was approximately 91%. The reaction mixture contained approximately 18.1 gram (91 mmol) of 2-chlorophenylalanine.

The supernatant (850 mL, pH 10.8) was concentrated under reduced pressure (150 to 10 mbar; bath temperature: 60° C.). After removal of about 65% of the water, a large quantity of precipitate was formed (pH 7.5). The precipitate was removed by filtration and stirred in water to remove inorganic salts. The resulting solid material was dried to give 14.9 g product. This product contained 57 w/w % (S)-2-amino-3-(2-chloro-phenyl)-propionic acid (8.5 g, 47% yield), 24 w/w % water and 1.7 w/w % 3-(2-chloro-phenyl)-acrylic acid. The e.e. of (S)-2-amino-3-(2-chloro-phenyl)-propionic acid was 99%. The mother liquid contained the remaining 9.5 g of (S)-2-amino-3-(2-chloro-phenyl)-propionic acid.

Step (iii): (S)-2,3-dihydro-1H-indole-2-carboxylic Acid: Conversion of (S)-2-amino-3-(2-chloro-phenyl)-propionic Acid with 1 mol % CuCl in Water at 95° C.

A flask was charged successively with 3.00 g (15.0 mmol) (S)-2-amino-3-(2-chloro-phenyl)-propionic acid, 2.17 g (15.7 mmol) K$_2$CO$_3$, 15 mg CuCl (2.9 mmol) and 15 g H$_2$O. The reactor was flushed with argon and then kept under a slow stream of argon. The reaction mixture was stirred and heated until 95° C. and kept at this temperature for 22 h. Samples were taken regularly and analyzed by HPLC. The conversion after 22 h was approximately 40%. Then 15 mL water was added and the mixture stirred and heated for an additional 18 h. HPLC indicated full conversion of (S)-2-chlorophenylalanine. The reaction mixture was cooled to ca 25° C. The pH of the solution was then decreased from 7.6 to ca 3.5. The precipitated (S)-2,3-dihydro-1H-indole-2-carboxylic acid was isolated by filtration and washed with 2×10 mL 0.01 M HCl. Found after drying 1.88 g (11.5 mmol) (S)-2,3-dihydro-1H-indole-2-carboxylic acid. Yield 76.6%, ee>99%.

The invention claimed is:

1. Process for the preparation of an enantiomerically enriched optionally substituted indoline-2-carboxylic acid according to formula (1)

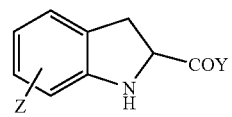

(1)

or a salt thereof, in which Y is an hydroxyl group, a substituted or non-substituted alkoxy group with 1-10 carbon atoms, a substituted or non-substituted aryloxy group or an amine residue, and in which Z represents one or more substituents on an aromatic group that are chosen from the group consisting of hydrogen, an hydroxyl group, an optionally substituted cyclic or acyclic aliphatic group with 1-10 carbon atoms, an optionally substituted aliphatic heterocyclic group with 1-10 carbon atoms, an optionally substituted (hetero)aryl group, an optionally substituted alkoxy group with 1-10 carbon atoms, a halogen atom, an amine group, a nitro group, a carboxylic acid, a carboxylic ester, a carboxylic amide, nitril and trifluoromethyl group, wherein an enantiomerically enriched chiral ortho-X-substituted phenylalanine compound according to formula (2)

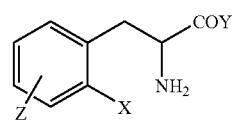

(2)

or a salt thereof, in which Y and Z are as defined above and X is a leaving group, is subjected to cyclisation at a temperature of below about 140° C., upon formation of the enantiomerically enriched indoline-2-carboxylic acid compound according to formula (1).

2. Process according to claim 1, wherein X is chosen from the group consisting of chloride, bromide, iodide, and a mesylate group.

3. Process according to claim 1, wherein Z is hydrogen, Y is hydroxyl and the indoline-2-carboxylic acid according to formula (1) is enantiomerically enriched in the (S)-enantiomer.

4. Process according to claim 1, wherein the process is carried out in the presence of a metal catalyst comprising a transition metal atom or ion selected from the groups 8 to 11 of the Periodic Table of Elements.

5. Process according to claim 1, wherein the metal catalyst comprises at least a copper metal atom or salt.

6. Process according to claim 1, wherein the process is carried out in the absence of a ligand.

7. Process according to claim 1, wherein the cyclisation reaction is carried out in an organic solvent, in water, in an ionic liquid or in a mixture of two or more thereof.

8. Process according to claim 1, wherein the cyclisation reaction is carried out in the presence of a base.

9. Process according to claim 1, wherein the enantiomerically enriched compound (2) is prepared from the corresponding ortho-X-substituted cinnamic acid derivative of formula (3)

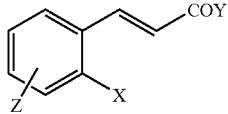
(3)

or a salt thereof, wherein X, Y and Z are as defined above, by reacting the compound of formula (3) with an amino group donor in the presence of a stereoselective phenylalanine ammonia lyase (PAL) [Process (A)].

10. Process according to claim 1, wherein the enantiomerically enriched compound (2) is prepared by contacting a compound according to formula (6)

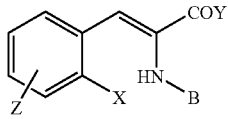
(6)

or a salt thereof, in which X, Y and Z are as defined above and B is a COR1 group in which R1 is an optionally substituted cyclic or acyclic aliphatic group with 1-10 carbon atoms, an optionally substituted aliphatic heterocyclic group with 1-10 carbon atoms, an optionally substituted (hetero)aryl group, or an optionally substituted alkoxy group with 1-10 carbon atoms, with a hydrogen donor in the presence of a chiral catalyst comprising a transition metal upon formation of a compound according to formula (7)

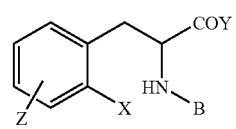
(7)

or a salt thereof, in which X, Y, Z and B are as defined above, and subjecting said compound (7) to an hydrolysis reaction upon formation of a compound according to formula (2) [Process (B)].

* * * * *